US00PP25415P3

(12) United States Plant Patent
Roberts

(10) Patent No.: US PP25,415 P3
(45) Date of Patent: Apr. 7, 2015

(54) MINT PLANT NAMED 'CHELAN MINT'

(50) Latin Name: *Mentha piperita*
Varietal Denomination: Chelan Mint

(71) Applicant: Essex Laboratories, Inc., Napavine, WA (US)

(72) Inventor: Donald D. Roberts, Independence, OR (US)

(73) Assignee: Essex Laboratories, Inc., Napavine, WA (US)

( * ) Notice: Subject to any disclaimer, the term of this patent is extended or adjusted under 35 U.S.C. 154(b) by 115 days.

(21) Appl. No.: 13/815,404

(22) Filed: Feb. 27, 2013

(65) Prior Publication Data

US 2014/0245509 P1 Aug. 28, 2014

(51) Int. Cl.
*A01H 5/00* (2006.01)

(52) U.S. Cl.
USPC ..... Plt./259

(58) Field of Classification Search
USPC ..... Plt./259
See application file for complete search history.

(56) References Cited

U.S. PATENT DOCUMENTS

PP11,788 P2 2/2001 Roberts
PP13,720 P2 4/2003 Roberts

OTHER PUBLICATIONS

Burbott, Alice J., et al., "Effects of Light and Temperature on the Monoterpenes of Peppermint," Plant Physiol., 1967, 42 , pp. 20-28.
Fuchs, Sabine, et al., "Biosynthesis of Menthofuran in *Mentha×piperita*; Stereoselective and Mechanistic Studies"; j. Agric. Food Chem., 1999, 47 (10), pp. 4100-4105.
Mahmoud, Soheil S., et al., "Methofuran regulates essential oil biosynthesis in peppermint by controlling a downstream monoterpene reductase," Proc. Natl. Acad. Sci, USA, Nov. 25, 2003; 100 (24) 14481-8.
Rohloff, Jens, et al., Effect of Harvest Time and Drying Method on Biomass Production, Essential Oil Yield, and Quality of Peppermint (*Mentha piperita* L.); J. Agric. Food Chem., 2005, 53 (10), pp. 4143-4148.

*Primary Examiner* — Susan McCormick Ewoldt
(74) *Attorney, Agent, or Firm* — Marger Johnson & McCollom, PC

(57) ABSTRACT

Mint selection 08-6-10, denominated 'Chelan Mint,' is a new *Mentha piperita* cultivar that produces a unique essential oil, a compact plant type and resistance to mint rust (*Puccinia menthae*) and mint wilt (*Verticillium dahlia*).

2 Drawing Sheets

Latin name of the genus and species: *Mentha piperita*.
Variety denomination: 'CHELAN MINT'.

FEDERAL SPONSORSHIP

None

TYPE OF PLANT AND NAME OF VARIETY

The present invention relates to a new and distinct variety of peppermint plant developed from a parent of the species *Mentha piperita* L. The new variety will be identified as 'Chelan Mint.'

BACKGROUND OF INVENTION

This plant was selected from a population of mint seedlings in research plots on land near Monmouth, Oreg. and initially identified as 08-6-10. 'Chelan Mint' originated as a seedling from an open pollinated polyploid 'Black Mitcham' parent identified as 05-4-9. Diploid 'Black Mitcham' peppermint is sterile and only becomes fertile in the polyploidy state. The fertile 'Black Mitcham' parent (05-4-9) to 'Chelan Mint' was one of several mint lines in a polycross breeding system composed of selected male and female fertile genotypes.

DISCOVERY AND ASEXUAL REPRODUCTION

The primary objective in this breeding program was to develop a Mitcham type peppermint variety having a specific oil composition, acceptable yield and resistant to mint wilt and mint rust. Mint wilt is caused by a soil-borne fungus, *Verticillium dahliae*, and mint rust is a leaf infection caused by the air-borne fungus *Puccinia menthae*. Only seedlings that showed no symptoms of mint wilt or rust were selected for further evaluation. 'Chelan Mint' was vegetative propagated by tip cuttings to increase the selection to 20 plants for continued evaluation in 2009. The selection was again vegetative propagated by stolon sections to over 300 plants for planting and evaluation in 2010. When compared to 'Black Mitcham' as a control, 'Chelan Mint' had less (or no) symptoms of mint wilt than the control and had no mint rust infection. Yield of 'Chelan Mint' is equivalent to 'Black Mitcham' in test plots as a single plant and in larger plot evaluations from 2009 to 2010.

'Chelan Mint' is asexually propagated to maintain the cultivar's genetic integrity and as a means of increasing the selection for commercial planting. Asexual propagation, by tip cuttings or stolon sections, is a common practice in commercial mint cultivation and serves as a means of propagating the normally sterile mint plant. The inventor has conducted asexual propagation of 'Chelan Mint' for greenhouse and field planting in Monmouth, Oreg., each year since 2008 and the genotype comes true to form with each generation.

SUMMARY OF THE INVENTION

Mint selection 08-6-10, denominated 'Chelan Mint,' is a new *Mentha piperita* cultivar that produces an essential oil different in composition than commercially grown mint varieties. The essential oil is similar to standard peppermint mint oil in component composition but differs in the typical ratio of components. Organoleptically it differs from typical peppermint oil. It is resistant to mint rust and more resistant to *Verticillium* mint wilt than current commercially grown varieties.

BRIEF DESCRIPTION OF THE FIGURES

The accompanying color figures show the typical one year old greenhouse vegetative growth of 'Chelan Mint' and depicts the color as nearly as reasonably possible.

FIG. 1 illustrates the growth and branching pattern of the new mint plant.

FIG. 2 illustrates the shape of the leaf and flower on a terminal flowering shoot.

DESCRIPTION OF PLANT

My new mint plant improves upon and is distinct from other mint plants in several characteristics, including but not limited to, the following:

1. The ability to produce an essential oil different in composition but with similar components as 'Black Mitcham' peppermint;
2. A more compact plant but with a branching pattern similar to its parent;
3. An early spring growth for a potential double harvest in one growing season;
4. A level of resistance to mint wilt (*Verticillium dahliae*) equal to or greater than that of its parent and the commercially grown 'Black Mitcham' peppermint.
5. Resistance to mint rust caused by *Puccinia menthae*.

The essential oil extracted from 'Chelan Mint' has the same components as that of commercial oil produced by 'Black Mitcham' peppermint as illustrated in Table 1. However, the ratio of oil components differs in the commercial peppermint oil and that of 'Chelan Mint.' The concentration of menthone in the oil of 'Chelan Mint' is lower than that of 'Black Mitcham.' The amount of Menthofuran and Menthyl Acetate in the oil of 'Chelan Mint' is higher than that of 'Black Mitcham.' The menthol has a similar concentration as that of 'Black Mitcham.' Organoleptically the oil of 'Chelan Mint' is different than that of 'Black Mitcham,' reflecting the difference in oil component ratios.

TABLE 1

Composition of 'Chelan Mint' Oil from Test Plots Compared to commercial 'Black Mitcham' Peppermint Oil and Oil from 'Black Mitcham' Peppermint Grown in Test Plots located near Monmouth, Oregon.

| Essential Oil Components | Commercial 'Black Mitcham' 1/ | 2008 Test Plot 'Black Mitcham' 2/ | 2008 Test Plot 'Chelan Mint' 3/ |
|---|---|---|---|
| α-pinene | 0.82 | 0.80 | <1.00 |
| β-pinene | 1.06 | 1.03 | <1.00 |
| l-limonene | 1.78 | 1.73 | 1.40 |
| 1,8-cineole | 5.33 | 4.90 | 4.20 |
| l-menthone | 20.00 | 19.43 | 10.00 |
| Menthofuran | 4.35 | 4.23 | 20.70 |
| Iso-menthone | 3.19 | 3.14 | 1.30 |
| l-menthyl acetate | 5.09 | 5.36 | 7.80 |
| Neo-menthol | 5.40 | 5.52 | 4.00 |
| B-caryophyllene | 0.83 | 0.85 | 1.60 |
| l-menthol | 45.20 | 44.60 | 44.20 |

TABLE 1-continued

Composition of 'Chelan Mint' Oil from Test Plots Compared to commercial 'Black Mitcham' Peppermint Oil and Oil from 'Black Mitcham' Peppermint Grown in Test Plots located near Monmouth, Oregon.

| Essential Oil Components | Commercial 'Black Mitcham' 1/ | 2008 Test Plot 'Black Mitcham' 2/ | 2008 Test Plot 'Chelan Mint' 3/ |
|---|---|---|---|
| Pulegone | 2.17 | 2.14 | <1.00 |
| Germacrene-D | 1.22 | 1.37 | <1.00 |

The numbers listed in the above table are percentages based upon the analysis of the respective mint oils by gas chromatography. The percentages are determined by calculation of the relative peak areas.

1/ Commercial oil sample typical of what is produced by peppermint producers.

2/ 'Black Mitcham' oil from a control plant in the 2008 seedling test plot.

3/ 'Chelan Mint' oil from a single plant harvest from the 2008 test plots.

TAXONOMIC DESCRIPTION OF 'CHELAN MINT'

This new plant, under greenhouse and field growing conditions, is a bush type plant with lateral branches at each node of the main stems. The average growth of 'Chelan Mint' in height is 50 cm and width is 25 cm but will vary based on fertilizer, soil quality, and water application, amongst other known factors that affect growth patterns. The main stem can grow to 70 cm in height. Secondary and tertiary branching occurs to form a compact growth habit. When 'Chelan Mint' is mature and ready for harvest, the main stem at mid-plant (approximately between the eleventh and twelfth node) is 3.3-3.9 mm in width. The secondary and tertiary branch stems are 2.2-2.7 mm and 1.5-2.0 mm in width, respectively. The average length of secondary branches is 12 cm. The tertiary branches, when present, are up to 6 cm in length. The stems are square, glabrous, and a green color illustrated by The Fifth Edition Royal Horticultural Society Colour Chart 143B green group, and has spots, randomly spaced, of anthocyanin pigment.

Mature leaves at the bottom of the plant are ovate to lanceolate as are leaves on secondary branch stems. Leaves on upper mature plants, both main and secondary stems are more lanceolate (FIG. 2). The adaxial leaf surface is glabrous. The abaxial leaf surface is sub-glabrous with oil glands distributed across the surface. Mid-main stem leaf size at flowering is 24-30 mm in width and 55-65 mm in length. Leaf size on secondary branches at flowering is 15-18 mm in width and 27-32 mm in length. Leaf petioles on the main stem leaves are 11-15 mm in length while petioles on secondary branch stem leaves are 4-6 mm in length. Leaves on the mid-main stem and lower tend to be slightly lobed and denticulate while the leaves on the upper plant tend to be more dentate. The main stem leaves have from 9 to 12 teeth on each side. The adaxial leaf surface is dark green in color, ranging from Fifth Edition Royal Horticultural Society Colour Chart N137B to N137C in the green group classification. The abaxial leaf surface is a green color as illustrated by Fifth Edition Royal Horticultural Society Colour Chart 146A, yellow green group. The leaf has 6-9 lateral veins, more or less in parallel off the main vain that runs from the petiole to the tip of the leaf. The veins are prominent in all leaves of 'Chelan Mint.'

The inflorescence is an inconspicuous raceme with capitate flowers developing at the last few nodes of the stem. The raceme varies in length from 7 to 10 cm and is influenced by environmental factors. The capitate flowers are 15-20 mm in width and 10-15 mm in length. The flowers consist of five petals fused into a two lipped corolla. The corolla is light in color ranging from Fifth Edition Royal Horticultural Society Colour Chart 84D in the Violet Group, to white in the Fifth Edition Royal Horticultural Society Colour Chart N155B white group. The Calyx is generally green and is 143B to 143C in the Fifth Edition Royal Horticultural Society Colour Chart, Green Group. The gynoecium consists of a single pistil with two lobed stigma that is exserted. The androecium consists of four stamens, each with a distinct filament and anther.

While the plant that comprises the present invention has been described in connection with a specific embodiment thereof, it will be understood that this application is intended to cover any variation, uses, or adaptation of the invention (particular those induced by cultivation under different environmental conditions) following, in general, the principles of the invention and including such departures from the present disclosure as come within known or customary practice in the art to which the invention pertains and as may be applied to the essential features hereinbefore set forth, and as fall within the scope of the invention and the limits of the appended claim.

I claim:

1. A new and distinct variety of peppermint plant, substantially as shown and described, characterized particularly by improving resistance to mint rust, and producing a unique essential oil.

* * * * *

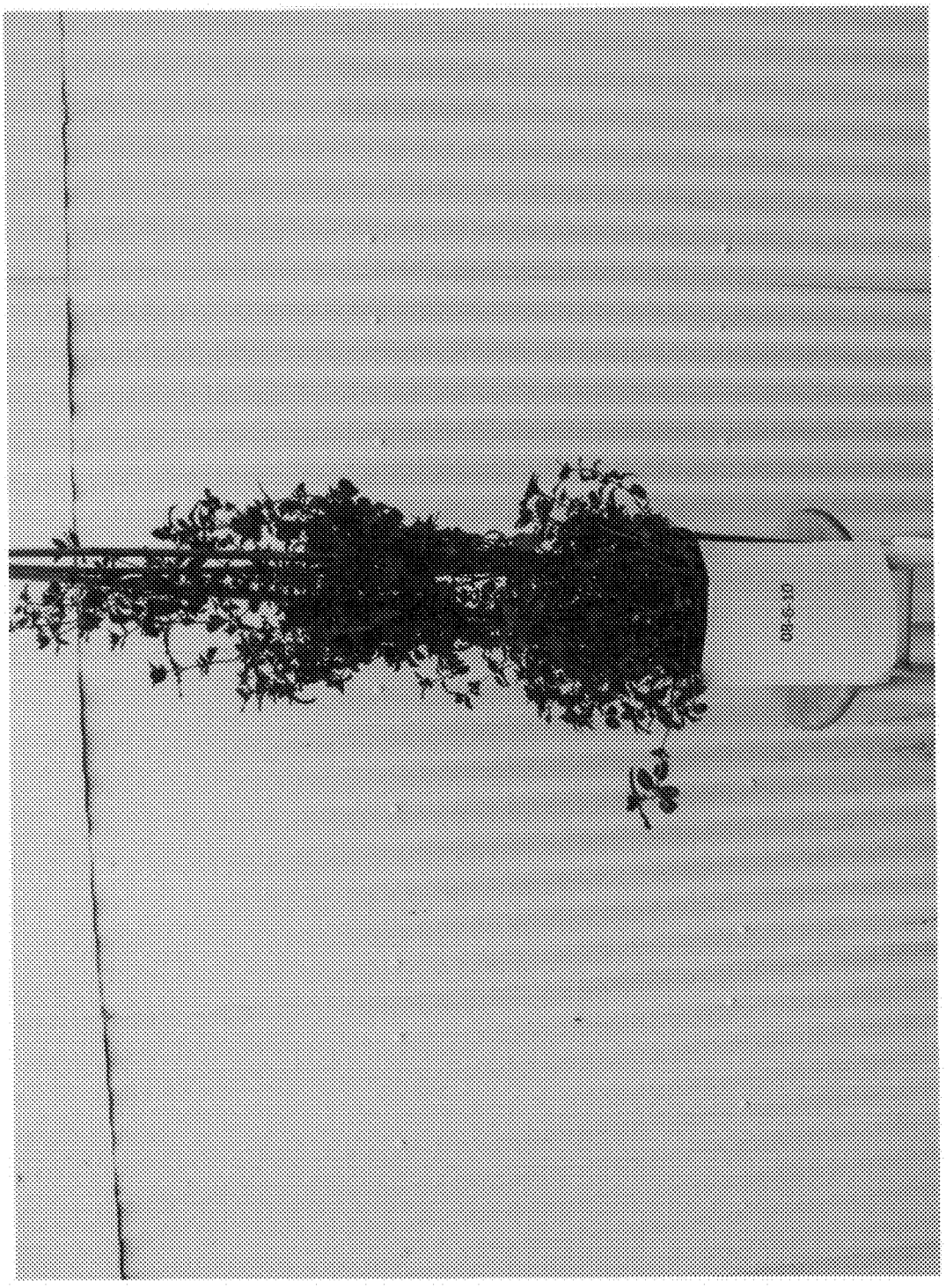

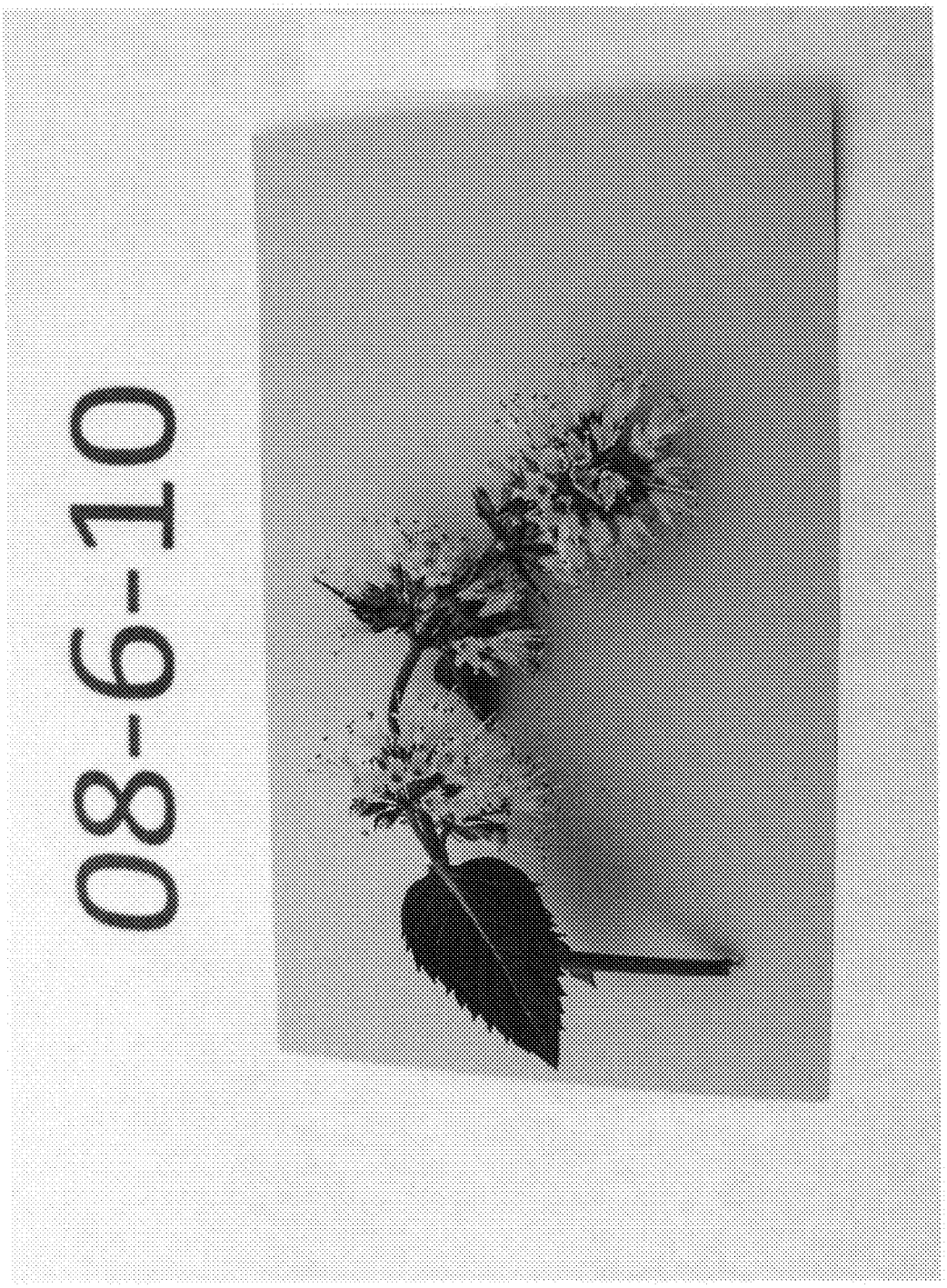
01-9-80